(12) United States Patent
Qian et al.

(10) Patent No.: US 8,476,050 B2
(45) Date of Patent: Jul. 2, 2013

(54) CONJUGATE PREPARATION METHODS AND RELATED KIT

(75) Inventors: Chungen Qian, Shenzhen (CN); Ke Li, Shenzhen (CN); Yuping Zhang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 78 days.

(21) Appl. No.: 13/152,083

(22) Filed: Jun. 2, 2011

(65) Prior Publication Data

US 2011/0300602 A1 Dec. 8, 2011

(30) Foreign Application Priority Data

Jun. 4, 2010 (CN) .......................... 2010 1 0192647

(51) Int. Cl.
*C12N 9/96* (2006.01)
*C07K 1/107* (2006.01)

(52) U.S. Cl.
USPC ..................... 435/188; 530/409; 530/391.7

(58) Field of Classification Search
USPC ............................... 435/188; 530/409, 391.7
See application file for complete search history.

(56) References Cited

U.S. PATENT DOCUMENTS

| | | | |
|---|---|---|---|
| 4,808,521 A | 2/1989 | Allen | |
| 5,093,231 A | 3/1992 | Hoke | |
| 5,674,980 A * | 10/1997 | Frankel et al. | 530/350 |
| 5,998,156 A * | 12/1999 | Sugiyama et al. | 435/7.92 |
| 6,218,160 B1 * | 4/2001 | Duan | 435/188 |
| 6,669,963 B1 | 12/2003 | Kampinga | |
| 6,767,716 B2 | 7/2004 | Giri | |
| 7,078,172 B1 | 7/2006 | Okamura et al. | |
| 2004/0197885 A1 | 10/2004 | Ueda et al. | |
| 2007/0141645 A1 | 6/2007 | Okamura et al. | |
| 2008/0254492 A1 | 10/2008 | Tsuchiya et al. | |
| 2009/0269825 A1 | 10/2009 | Kishimoto et al. | |
| 2011/0159565 A1 | 6/2011 | Qian et al. | |
| 2011/0300601 A1 | 12/2011 | Qian et al. | |

FOREIGN PATENT DOCUMENTS

| | | |
|---|---|---|
| CN | 1120457 | 4/1996 |
| CN | 1381725 | 11/2002 |
| CN | 1683407 | 10/2005 |
| CN | 1986785 | 6/2007 |
| CN | 100353166 | 12/2007 |
| EP | 0709458 | 5/1996 |
| EP | 0794249 | 9/1997 |
| EP | 0702712 | 12/1998 |
| EP | 1978363 | 2/2008 |
| JP | 2003009857 | 1/2003 |
| WO | WO2007055284 | 5/2007 |

OTHER PUBLICATIONS

Journal of Nanton Medical College 1996:16(2); pp. 162-164, with English abstract.
U.S. Appl. No. 13/151,876, filed Jun. 2, 2011, Qian et al.
Restriction Requirement dated Jul. 11, 2012 for U.S. Appl. No. 12/980,870.
Office Action dated Oct. 26, 2012 for U.S. Appl. No. 12/980,870.
Govardhan, 'Crosslinking to Enzymes for Improved Stability and Performance', Current Opinion Biotechnol, vol. 10, pp. 331-335, 1999.
Beiniarz et al., 'Alkaline Phosphatase Activatable Polymeric Cross-Linkers and Their Use in the Stabilization of Proteins', Bioconjugate Chemistry, vol. 9, pp. 390-398, 1998.
Beiniarz et al., 'Technical Notes: Thermally Stabilized Immunoconjugates: Conjugation of Antibodies to Alkaline Phsphatase Stabilized with Polymeric Cross-Linkers', Bioconjugate Chemistry, vol. 9, pp. 399-402, 1998.

* cited by examiner

*Primary Examiner* — Chih-Min Kam
(74) *Attorney, Agent, or Firm* — Kory D. Christensen; Stoel Rives LLP (57) ABSTRACT

Methods for preparing conjugates including enzyme conjugates and especially alkaline phosphatase (ALP) conjugates, and a kit are provided. The methods include: blocking an amino group on a molecule surface of a first substance to be conjugated containing an amino group and a carboxyl group (for example, an enzyme) with a carboxyl compound; adding a carbodiimide to activate the first substance to be conjugated with the amino group blocked; inactivating or removing the carbodiimide; and adding a second substance containing an amino group (for example, a substance to be labeled). Conjugates (for example, enzyme conjugates) are obtained.

22 Claims, 2 Drawing Sheets

CONJUGATE PREPARATION METHODS AND RELATED KIT

RELATED APPLICATIONS

This application claims priority to Chinese Patent Application No. 201010192647.0, filed Jun. 4, 2010, for "CONJUGATE PREPARATION METHODS AND RELATED KIT," the disclosure of which is fully incorporated herein by reference.

TECHNICAL FIELD

The present disclosure relates to the field of immunoassays, and particularly to methods for preparing conjugates such as enzyme conjugates, and especially alkaline phosphatase (ALP) conjugates, and a kit applied thereto.

DETAILED DESCRIPTION

Enzyme conjugates include, for example, enzyme-antigen conjugates, enzyme-antibody conjugates, and enzyme-Staphylococal Protein A (SPA) conjugates. The quality of the enzyme conjugates is directly related to the success of enzyme immunoassay. The most frequently used enzyme conjugates are enzyme-antibody conjugates, which are formed by conjugating enzymes to specific antibodies through appropriate methods. Enzyme-antibody conjugates are mainly used in immunoassay and quantitative analysis such as Western blotting, enzyme linked immunosorbent assay (ELISA), chemiluminescence enzyme immunoassay (CLEIA), and immunohistochemistry. The quality of enzyme-antibody conjugates depends on the purity, activity, and affinity of enzymes and antibodies used, as well as good preparation methods.

Presently, methods for preparing enzyme-antibody conjugates or enzyme-antigen conjugates mainly include the following three types (see, Bioconjugate Techniques, Academic Press/2008, the $2^{nd}$ edition).

1. Glutaraldehyde (GA) Cross-Linking Method

In this method, an enzyme is bound to an antibody or antigen with a bifunctional cross-linking agent as a bridge. The most commonly used cross-linking agent is GA. GA includes two active aldehyde groups, which can be bound respectively to amino groups on an enzyme and an antibody or antigen. The GA method may comprise a one-step reaction or a two-step reaction depending on the manner in which reagents are added. In the one-step method, glutaraldehyde may be added directly into a mixture of an enzyme and a substance to be labeled to obtain an enzyme conjugate after reaction. In the two-step method, an enzyme may first be reacted with glutaraldehyde, then dialyzed to remove excess glutaraldehyde, and second, reacted with a substance to be labeled to form the enzyme conjugate. Alternatively, a substance to be labeled may be first reacted with glutaraldehyde, and then linked to an enzyme. ALP conjugates may be obtained using this method. The activity and the binding rate of the ALP conjugates synthesized using these methods may be unacceptable, however, which can reduce the sensitivity of immunoassays performed using an ALP conjugate made via this method.

2. Oxidation with a Periodate

This method can be used with enzymes having a high saccharide content. Horseradish peroxidase conjugates may be made by this method. In this reaction, polysaccharide hydroxyl groups on the surface of the horseradish peroxidase molecule are oxidized by sodium periodate to highly reactive aldehyde groups. The aldehyde groups can react with amino groups on substance to be conjugated to form a Schiff base. The substance is thus conjugated with the horseradish peroxidase. However, this method may be complicated and enzyme, antibody, or antigen activity may be lost or reduced after labeling.

3. Succinimide-Maleimide Crosslinking Methods

A heterologous bifunctional crosslinking reagent having a succinimide ester capable of reacting with an amino group, as well as a maleimide group capable of reacting with a mercapto group, may be used in the preparation of an ALP conjugate. Crosslinking reagents of this type include 4-(N-maleimidomethyl)cyclohexane-1-carboxylate N-hydroxysuccinimide ester (SMCC) and a water soluble analog thereof, 4-(N-Maleimidomethyl)cyclohexane-1-carboxylate sulfo-N-hydroxysuccinimide ester (sulfo-SMCC). These crosslinking reagents can activate an amino group on the ALP, to obtain an ALP having a maleimide group, and the maleimide group can then react with a mercapto group on the substance to be conjugated, to obtain an ALP conjugate. However, the reagents used for these methods can be expensive, and the substance to be conjugated generally needs to be thiolated.

The present disclosure provides a method for preparing a conjugate such as an enzyme conjugate, and especially an ALP conjugate, and a kit. The method is simple and inexpensive, and the activity of conjugate constituent, for example, the enzyme and the substance to be labeled is maintained, and reagent made by the enzyme conjugate has high sensitivity.

In one aspect, the present disclosure relates to a method for preparing a conjugate from a first substance to be conjugated and a second substance to be conjugated, wherein the first substance to be conjugated contains an amino group and a carboxyl group, and the second substance to be conjugated contains an amino group, and the method includes:

1) blocking the amino group of the first substance to be conjugated with a carboxyl compound having the following general formula I, in the presence of a first cross-linking agent:

wherein $R_1$ is selected from at least one of following: H, $C_{1-6}$ alkyl, $C_nH_{2n}COOH$, phenyl, and phenyl$C_{1-6}$ alkyl, wherein n is an integer of 0-4, and phenyl or phenyl$C_{1-6}$ alkyl is optionally and independently substituted with a substitution group selected from at least one of the following: halogen, hydroxyl, mercapto, cyano, nitro, alkyl, aryl, alkoxy, heterocyclyl, haloalkyl, and carboxyl; and $R_2$ is a group which is capable of dissociating in water, such as H, Na, or K;

and wherein the cross-linking agent comprises a carbodiimide and, optionally, a hydroxysuccinimide;

2) purifying the first substance to be conjugated with the amino group blocked;

3) adding a second cross-linking agent to activate the carboxyl group of the purified first substance to be conjugated with the amino group blocked, wherein the cross-linking agent comprises a carbodiimide and, optionally, a hydroxysuccinimide; and 4) cross-linking the activated first substance to be conjugated and the second substance to be conjugated.

In an embodiment of this aspect, the conjugate is an enzyme conjugate, and the first substance to be conjugated is an enzyme for labeling.

In another embodiment, the conjugate is an enzyme conjugate, the first substance to be conjugated is a peptide or a protein, for example, an antibody; and the second substance to be conjugated is an enzyme for labeling.

In the above two embodiments, the enzyme for labeling is selected from at least one of the following: ALP, horseradish peroxidase, β-galactosidase, urease, glucose-6-phosphate dehydrogenase, glucose oxidase, and malate dehydrogenase.

In a third embodiment, the first substance to be conjugated is a carrier protein, and the second substance to be conjugated is a hapten.

In a fourth embodiment, the first substance to be conjugated is a peptide or a protein, and the second substance to be conjugated is a solid phase.

In a fifth embodiment, the first substance to be conjugated is a targeting moiety selected from at least one of the following: an antibody and a ligand, and the second substance to be conjugated is a drug containing an amino group; or the first substance to be conjugated is a peptide or protein drug, and the second substance to be conjugated is a targeting moiety selected from at least one of the following: an antibody and a ligand.

In the above embodiments, after the carboxyl group of the first substance to be conjugated is activated, the activity of the cross-linking agent may be quenched by adding a mercapto compound, or removing the cross-linking agent through purification, to obtain the first substance to be conjugated with an activated carboxyl group and a blocked amino group.

In the above embodiments, the first substance to be conjugated with a blocked amino group, or the first substance to be conjugated with an activated carboxyl group and a blocked amino group may be purified by ultrafiltration, desalting column purification, and/or dialysis purification.

In one embodiment, the carboxyl compound may be selected from at least one of the following: formic acid, acetic acid, oxalic acid, benzoic acid, salicylic acid, sulfosalicylic acid, and a salt thereof. In one embodiment, the carboxyl compound is selected from at least one of the following: formic acid, acetic acid, oxalic acid, benzoic acid, and a salt thereof. And in another embodiment, the carboxyl compound is sodium acetate.

In one embodiment, the carbodiimide may be selected from at least one of the following: dicyclohexylcarbodiimide, 1-(3-dimethylaminopropyl)-3-ethylcarbodiimide, and N,N'-diisopropylcarbodiimide; and the hydroxysuccinimide may be selected from at least one of the following: N-hydroxysuccinimide and sulfo-N-hydroxysuccinimide.

In Step 1), the mole number of the carboxyl compound may be 500-200000 times, or 1000-20000 times that of the first substance to be conjugated. The mole number of the cross-linking agent may also be 50-5000 times, or 100-1000 times that of the first substance to be conjugated. The molar ratio of the carbodiimide to the hydroxysuccinimide may be in a range of between 5:1 to 1:10, or 2:1 to 1:5.

In Step 3), the mole number of the carbodiimide may be 10-5000 times, or 50-1000 times that of the first substance to be conjugated with the amino group blocked; and the molar ratio of the carbodiimide to the hydroxysuccinimide may be in a range of between 5:1 to 1:10, or 2:1 to 1:5.

The mercapto compound may be selected from at least one of the following: mercapto ethanol and mercapto threitol.

In another aspect, the present disclosure is directed to a kit for preparing enzyme conjugates, comprising:

1) an enzyme for labeling, selected from at least one of the following: ALP, horseradish peroxidase, β-galactosidase, urease, glucose-6-phosphate dehydrogenase, glucose oxidase, pyruvate kinase, and malate dehydrogenase;

2) a carboxyl compound having general formula I:

I where $R_1$ is selected from at least one of the following: H, $C_{1-6}$ alkyl, $C_nH_{2n}COOH$, phenyl, and phenyl$C_{1-6}$ alkyl, wherein n is an integer of 0-4, and phenyl or phenyl$C_{1-6}$ alkyl is optionally and independently substituted with a substitution group selected from at least one of the following: halogen, hydroxyl, mercapto, cyano, nitro, alkyl, aryl, alkoxy, heterocyclyl, haloalkyl, and carboxyl; and $R_2$ is a group which is capable of dissociating in water, such as H, Na, or K;

3) a crosslinking agent, comprising a carbodiimide and, optionally, a hydroxysuccinimide; and 4) an optional mercapto compound.

In one embodiment, the carboxyl compound may be selected from at least one of following: formic acid, acetic acid, oxalic acid, benzoic acid, salicylic acid, sulfosalicylic acid, and a salt thereof.

In one embodiment, the carbodiimide may be selected from at least one of the following: dicyclohexylcarbodiimide, 1-(3-dimethylaminopropyl)-3-ethylcarbodiimide, and N,N'-diisopropylcarbodiimide; and the hydroxysuccinimide may be selected from at least one of the following: N-hydroxysuccinimide and sulfo-N-hydroxysuccinimide.

In one embodiment, the mercapto compound may be selected from at least one of the following: mercapto ethanol and mercapto threitol.

In one embodiment, the kit may further contain an ultrafiltration tube, a manual which instructs an operator, or both.

The present disclosure provides methods for preparing conjugates, particularly enzyme conjugates, and more particularly ALP conjugates. According to the present disclosure, an amino group on the molecular surface of a first substance to be conjugated (for example, an enzyme) containing an amino group and a carboxyl group is blocked with a carboxyl compound and the carboxyl group in the first substance to be conjugated is activated with a carbodiimide after the carboxyl compound is removed. Then the carbodiimide is inactivated or removed, and a second substance to be conjugated (for example, a substance to be labeled) having an amino group is added, and the activated carboxyl in the first substance to be conjugated reacts with the amino group in the second substance to be conjugated to obtain a conjugate (for example, an enzyme conjugate). First blocking the amino group on the surface of the first substance to be conjugated may effectively reduce self-cross-linking, which may improve the activity and labeling rate of the conjugate (for example, the enzyme conjugate). As shown in the examples below, compared with an enzyme conjugate obtained by a conventional method (such as the GA method or the sodium periodate method), the activity of ALP conjugates prepared by the methods of the present disclosure is obviously improved. Additionally, the methods of the present disclosure use a relatively inexpensive carboxyl compound, and the carboxyl group for blocking the amino group does not need to be removed from conjugates, so the operation is simple and easy, and the cost is low.

In the present disclosure, the first substance to be conjugated may include compounds containing an amino group and a carboxyl group, or compounds to which the groups are introduced through modification, for example, a hapten, an antigen, an antibody, and other peptide or protein substances, such as, an enzyme, a ligand, a carrier protein, a peptide or protein drug.

In the present disclosure, the second substance to be conjugated may include compounds having an amino group, or compounds to which the amino group is introduced through modification, for example, a substance to be labeled including a peptide or a protein, such as an antigen, a hapten, an enzyme, a ligand, a peptide or protein drug, and a solid phase containing an amino group.

The enzyme as used herein may be any enzyme for labeling, available from various sources, and useful in enzyme immunoassays (including CLEIA, ELISA, and Western blotting), and includes enzymes for labeling which are naturally extracted or prepared through bioengineering modifications, such as, ALP, horseradish peroxidase, β-galactosidase, urease, glucose-6-phosphate dehydrogenase, glucose oxidase, pyruvate kinase, and malate dehydrogenase.

ALP as used herein may be obtained from various animal sources. It may also be obtained by different ways, such as natural extraction or bioengineering modifications.

The substance to be labeled as used herein includes a compound to be labeled containing an amino group, and a compound to be labeled to which an amino group is introduced through amino modification, for example, a small-molecule hapten, an antigen, or an antibody containing an amino group. The small-molecule hapten may be triiodothyronine, thyroxine, or a peptide.

Antibodies as used herein include various animal derived monoclonal antibodies, polyclonal antibodies, and antibody fragments, and also include different types of antibodies, for example, immunoglobulin G, immunoglobulin A, immunoglobulin E, immunoglobulin M, immunoglobulin D, and immunoglobulin Y.

The carbodiimide as used herein is a chemically active bifunctional reagent, which dehydrates a carboxyl group and an amino group to form an amido bond. A carboxyl group on a protein or peptide firstly reacts with the carbodiimide to generate an intermediate, and then reacts with an amino group on another protein or peptide, to form a conjugate of proteins or peptides. Using this cross-linking method, the activity of the protein or peptide may be better retained after cross-linking, and cross-linking efficiency may be relatively higher. The carbodiimide may be dicyclohexylcarbodiimide (DCC), 1-(3-dimethylaminopropyl)-3-ethylcarbodiimide (EDC), or N,N'-diisopropylcarbodiimide (DIC).

The hydroxysuccinimide as used herein may improve the yield of the carbodiimide cross-linking reaction, and reduce the occurrence of side reactions. The hydroxysuccinimide may be N-hydroxysuccinimide (NHS), or sulfo-N-hydroxysuccinimide (sulfo-NHS).

The carboxyl compound as used herein is a water soluble compound capable of dissociating in an aqueous solution to generate a carboxylate ion. The carboxyl compound contains at least one carboxylate radical, and has a structure of General Formula I below:

where $R_1$ is selected from at least one of the following: H, $C_{1-6}$ alkyl, $C_nH_{2n}COOH$, phenyl, and phenyl$C_{1-6}$ alkyl, wherein n is an integer of 0-4, and phenyl or phenyl$C_{1-6}$ alkyl is optionally and independently substituted with a substitution group selected from at least one of the following: halogen, hydroxyl, mercapto, cyano, nitro, alkyl, aryl, alkoxy, heterocyclyl, haloalkyl, and carboxyl; and $R_2$ is a group which is capable of dissociating in water, such as H, Na, or K.

The carboxyl compound having a structure of General Formula I may be formic acid, acetic acid, oxalic acid, benzoic acid, salicylic acid, sulfosalicylic acid, or a salt thereof.

Figure 1:
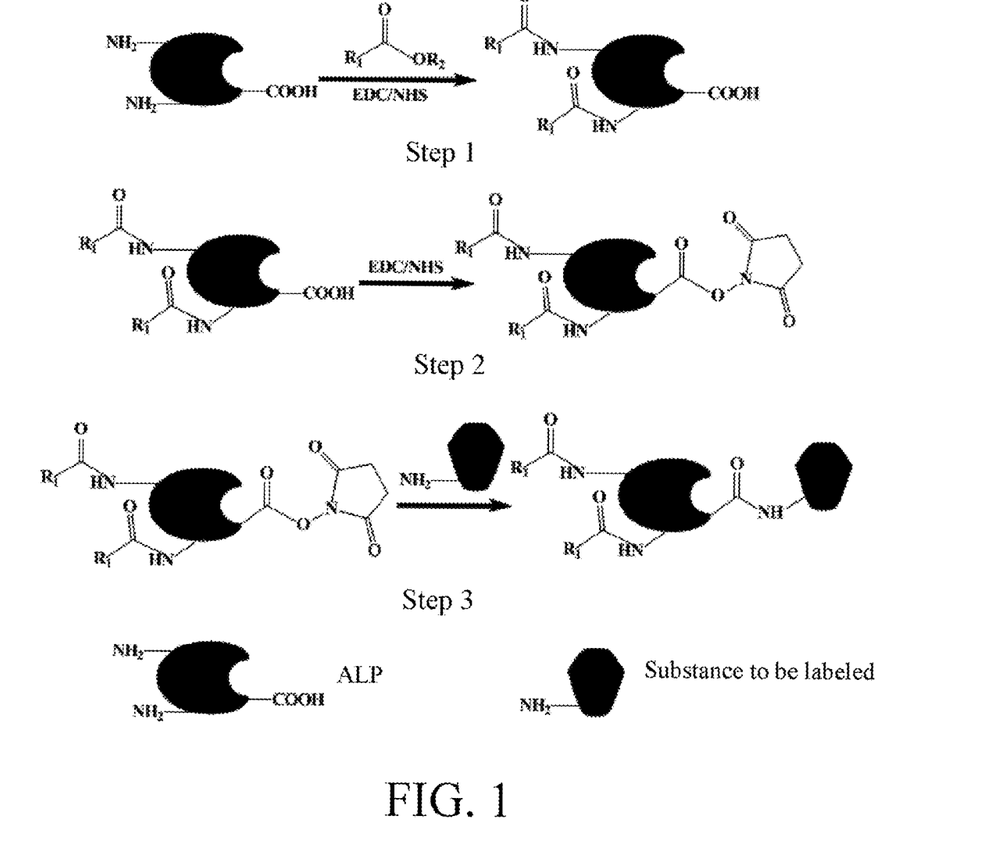
FIG. 1 shows a reaction scheme for an embodiment of the methods according to the present disclosure.

Enzyme conjugates are used as an example to illustrate the method of the present disclosure. As shown in FIG. 1, in Step 1), an amino group of an enzyme molecule is blocked; in Step 2), a carboxyl group of the enzyme with the amino group blocked is activated; and in Step 3), the activated enzyme molecule and a substance to be labeled are cross-linked.

In Step 1), a cross-linking agent and an enzyme are added in a buffer containing an excess of carboxyl compound to perform a blocking reaction. In some embodiments, the enzyme may be added within 1 hour (for example, 5 to 60 min, such as 15 to 30 min) after the cross-linking agent is added. The enzyme is then purified to obtain an enzyme molecule with a blocked amino group. In this step, a carboxyl group of the carboxyl compound which is activated by the cross-linking agent reacts with the amino group on the enzyme, so as to block the amino group. As the amount of carboxyl compound is much larger than that of enzyme, activation of the enzyme's carboxyl group by the cross-linking reagent is inhibited. In this step, the reaction occurs between pH4 and pH8. The buffer may be a phosphate buffer, a 2-(N-morpholino)ethane sulfonic acid (MES) buffer, and a piperazine-N,N' bis(2-ethanesulfonic acid) (PIPES) buffer. In some embodiments, the mole number of the carboxyl compound is 500-200000 times more than that of enzyme, for example, 1000-20000 times. The cross-linking agent may be a carbodiimide, or a carbodiimide and a hydroxysuccinimide. The cross-linking agent may be used in a wide concentration range, its amount may be 50-5000 times, such as 100-1000 times more than that of enzyme. In some embodiments, the molar ratio of the carbodiimide to the hydroxysuccinimide is in a range of between 5:1 to 1:10, and, for example, 2:1 to 1:5. Proteins are usually unstable at high temperature, so the reaction temperature is generally in a range of between 4° C. to 37° C. The blocking time is from 0.5 to 48 hours, and the skilled person will understand the relationship between reaction temperature and reaction time, and that the reaction time can be correspondingly shortened by raising the reaction temperature. Purification may be by ultrafiltration purification, desalting column purification, or dialysis purification.

In Step 2), the purified enzyme molecule with the amino group blocked obtained in Step 1) is added into a buffer, then a cross-linking agent is added. After allowing the reaction to proceed for 5-60 minutes, a mercapto compound is added to quench the activity of the cross-linking agent, or the cross-linking agent is removed by purification, to obtain an enzyme with the carboxyl group activated and the amino group blocked. In one embodiment of this step, the pH of the reaction is in a range of between 4 to 8. The buffer may be, for example, a phosphate buffer, an MES buffer, or a PIPES buffer. In one embodiment, the cross-linking agent is a carbodiimide, or a carbodiimide and a hydroxysuccinimide. The mole number of the carbodiimide may be 10-5000 times, such as 50-1000 times more than that of enzyme; and the molar ratio of the carbodiimide to the hydroxysuccinimide may be 5:1 to 1:10, for example, 2:1 to 1:5. In one embodiment, the reaction temperature is between 4° C. to 37° C.; and reaction time is from 5 to 300 minutes. The mercapto compound may be mercapto ethanol or mercapto threitol. In one embodiment, the mercapto compound is mercapto ethanol. The working concentration of the mercapto compound is between 5 mM to 50 mM. The enzyme with the carboxyl group activated and the amino group blocked may be purified by ultrafiltration purification, desalting column purification, and dialysis purification.

In Step 3), the enzyme that is obtained in Step 2), wherein the carboxyl group is activated and the amino group is blocked, is added into a buffer containing a substance to be labeled, to obtain an enzyme conjugate after reaction, or further obtain a purified enzyme conjugate after purification. In one embodiment of this step, the pH value of the reaction is in a range of 4 to 8.5. The buffer may be, for example, a phosphate buffer, a carbonate buffer, an MES buffer, a PIPES buffer, a 3-(N-morpholino)propane sulfonic acid (MOPS) buffer, or an N-2-hydroxyethylpiperazine-N-2-ethane sulfonic acid (HEPES) buffer. The molar ratio of the enzyme molecules to the substance to be labeled is 5:1 to 1:15; the reaction temperature is between 4° C. to 37° C.; and the reaction time is from 0.5 to 36 hours. The enzyme conjugate may be purified by gel filtration purification, Protein A or G affinity column purification, or ammonium sulfate precipitation methods.

Other enzyme conjugates, such as glucose oxidase conjugates may also be prepared by the methods of the present disclosure. Glucose oxidase contains multiple amino groups, and will easily become widely polymerized when used for labeling using existing methods, thus affecting the activity of the enzyme. When glucose oxidase conjugates are prepared by the methods of the present disclosure, self-crosslinking of glucose oxidase may be reduced, thus improving its activity.

In view of the present disclosure, it can be understood that the amino groups of the substance to be labeled may be blocked with a carboxyl compound first, and then the substance to be labeled is cross-linked with the enzyme using a cross-linking agent.

The methods and kits of the present disclosure may be used to prepare an artificial antigen of a hapten containing an amino group. Using the methods of the present disclosure, an amino group of a carrier protein is blocked with a carboxyl compound first, and then the carrier protein is cross-linked to a hapten using a crosslinking agent.

The methods and kits of the present disclosure may also be used to prepare a targeting drug, as long as the step of blocking amino groups of the targeting moiety or the peptide or protein drug moiety does not influence the targeting or drug efficacy. For example, in one embodiment, the amino group of the protein or peptide targeting moiety (such as, an antibody or a ligand) may be blocked with a carboxyl compound, and then the protein or peptide targeting moiety is cross-linked with a drug containing an amino group or to which an amino group is introduced through chemical modification by using a cross-linking agent. Alternatively, the amino group of the protein or peptide drug moiety is blocked first, and then the protein or peptide drug moiety is cross-linked with a targeting moiety (such as, an antibody or a ligand).

The methods and kits of the present disclosure may further be used to link a protein (including an antibody and an enzyme) or a peptide to an amino group-containing surface, for example, a solid phase. An amino group of a protein or peptide may be blocked by a carboxyl compound first, and then the protein or peptide is linked to the amino group-containing surface using a cross-linking agent.

Hereinafter, ALP conjugates are used as an example to illustrate the present disclosure; however, the scope of the present disclosure is not limited thereto. In the examples below, unless indicated otherwise, the reagents used are all analytical grade purity and obtained from Sigma-Aldrich Company.

EXAMPLES

Example 1

Sodium acetate was dissolved in 800 μl of 30 mM MES buffer (pH 6.0), EDC and NHS were added, and then buffer was added until the volume of the solution was 1000 μl, wherein the final concentrations of sodium acetate, EDC, and NHS were 1.8 mol/L, 18 mmol/L, and 18 mmol/L respectively. The solution was reacted at 22° C. for 30 minutes, and then 2 mg of ALP (about 18 nmol) and 2 ml of 0.1 M phosphate buffer (pH 7.2) were added. After 3 hours at 22° C., the reaction solution was ultra filtered 3 times in a 15 ml ultrafiltration tube (Millipore Company) whose cut-off molecular weight was 30 kDa, with 30 mM MES buffer (pH 6.0) as a replacement buffer. In this way, unreacted sodium acetate, EDC, NHS, and by-products were removed to obtain a solution of ALP with the amino group blocked.

EDC and NHS were then added into 1 ml of a 10 mmol/L solution of ALP with the amino group blocked, wherein the final concentration of EDC and NHS were 10 mmol/L and 20 mmol/L respectively. After 30 minutes at 22° C., mercapto ethanol was added to a final concentration of 10 mM to stop the reaction, yielding a solution of ALP with the carboxyl group activated and the amino group blocked.

Then, 1.5 mg of goat anti-thyroid stimulating hormone (TSH) polyclonal antibody (about 10 nmol) and 2 ml of 0.1 M phosphate buffer (pH 7.2) were added to the solution of ALP with the carboxyl group activated and the amino group blocked. After 3 hours at 37° C., the resulting enzyme-antibody conjugate was purified from the solution with a Protein G affinity column (GE Company), yielding a solution of goat anti-TSH polyclonal antibody-ALP conjugate.

Example 2

Acetic acid was dissolved in 2000 μl of 30 mM MES buffer (pH 5.0), and the pH value was adjusted to 5.0. EDC, NHS, and 2 mg of ALP (about 18 nmol) were added, and then 30 mM MES buffer (pH 5.0) was added until the volume of the solution was 3000 μl, wherein the final concentrations of acetic acid, EDC, NHS, and ALP were 0.06 mol/L, 24 mmol/L, 6 mmol/L, and 6 μmol/L respectively. After 30 minutes at 22° C., the reaction solution was ultra filtered 3 times in a 15 ml ultrafiltration tube (Millipore Company) whose cut-off molecular weight was 30 kDa, with 30 mM MES buffer (pH 6.0) as a replacement buffer. In this way, unreacted acetic acid, EDC, NHS, and by-products were removed to obtain a solution of ALP with the amino group blocked.

EDC and NHS were added to 1 ml of a 10 mmol/L solution of ALP with the amino group blocked, wherein the final concentration of EDC and NHS were 5 mmol/L and 25 mmol/L respectively. After 60 minutes at 22° C., mercapto ethanol was added to a final concentration of 10 mM to stop the reaction, yielding a solution of ALP with the carboxyl group activated and the amino group blocked.

Then, 0.75 mg of goat anti-TSH polyclonal antibody (about 5 nmol) and 2 ml of 0.1 M HEPES buffer (pH 8.0) were added to the solution of ALP with the carboxyl group activated and the amino group blocked. After 3 hours at 37° C., the enzyme-antibody conjugate was purified from the solution with a Protein G affinity column (GE Company), yielding a solution of goat anti-TSH polyclonal antibody-ALP conjugate.

Example 3

Formic acid was dissolved in 800 µl of 30 mM MES buffer (pH 6.0), the pH value was adjusted to 6.0. EDC and NHS were added, and then buffer was added until the volume of the solution was 1000 µl, wherein the final concentrations of formic acid, EDC, and NHS were 13.5 mmol/L, 0.36 mmol/L, and 1.8 mmol/L respectively. After 5 minutes at 37° C., 2 mg (about 18 nmol) of ALP and 2 ml of 0.1 M phosphate buffer (pH 7.2) were added into the solution. After 20 hours at 4° C., the reaction solution was ultra filtered 3 times in a 15 ml ultrafiltration tube (Millipore Company) whose cut-off molecular weight was 30 kDa, with 30 mM MES buffer (pH 6.0) as a replacement buffer. In this way, unreacted formic acid, EDC, NHS, and by-products were removed to obtain a solution of ALP with the amino group blocked.

EDC and NHS were added to 1 ml of a 10 mmol/L solution of ALP with the amino group blocked, wherein the final concentration of EDC and NHS were 10 mmol/L and 20 mmol/L respectively. After 10 minutes at 37° C., mercapto ethanol was added to a final concentration of 10 mM to stop the reaction, yielding a solution of ALP with the carboxyl group activated and the amino group blocked.

Then, 3 mg of goat anti-TSH polyclonal antibody (about 20 nmol) and 2 ml of 0.1 M phosphate buffer (pH 7.2) were added to the solution of ALP with the carboxyl group activated and the amino group blocked. After 24 hours at 4° C., the enzyme-antibody conjugate was purified with a Protein G affinity column (GE Company), yielding a solution of goat anti-TSH polyclonal antibody-ALP conjugate.

Example 4

Sodium acetate was dissolved in 800 µl of 30 mM MES buffer (pH 5.5), EDC was added, and then buffer was added until the volume of the solution was 1000 µl, wherein final concentrations of sodium acetate and EDC were 3.6 mol/L and 90 mmol/L respectively. After 30 minutes at 22° C., 2 mg of ALP (about 18 nmol) and 2 ml of 0.1 M phosphate buffer (pH 7.2) were added. After 3 hours at 22° C., the reaction solution was ultra filtered 3 times in a 15 ml ultrafiltration tube (Millipore Company) whose cut-off molecular weight is 30 kDa, with 30 mM MES buffer (pH 6.0) as a replacement buffer. In this way, unreacted sodium acetate, EDC, and by-products were removed to obtain a solution of ALP with the amino group blocked.

EDC and NHS were added to 1 ml of a 10 mmol/L solution of ALP with the amino group blocked, wherein the final concentration of EDC and NHS were 2 mmol/L and 20 mmol/L respectively. After 30 minutes at 22° C., the reaction solution was ultra filtered 3 times in a 15 ml ultrafiltration tube (Millipore Company) whose cut-off molecular weight was 30 kDa, with 30 mM MES buffer (pH 6.0) as a replacement buffer. In this way, unreacted EDC and NHS were removed to yield a solution of ALP with the carboxyl group activated and the amino group blocked.

Then, 0.45 mg of goat anti-TSH polyclonal antibody (about 3 nmol) and 2 ml of 0.1 M phosphate buffer (pH 7.2) were added to the solution of ALP with the carboxyl group activated and the amino group blocked. After 2 hours at 37° C., the enzyme-antibody conjugate was purified from the solution with a Protein G affinity column (GE Company), yielding a solution of goat anti-TSH polyclonal antibody-ALP conjugate.

Example 5

Benzoic acid was dissolved in 800 µl of 30 mM MES buffer (pH 6.0), the pH value was adjusted to 6.0. EDC and NHS were added, and then buffer was added until the volume of the solution was 1000 µl, wherein final concentrations of benzoic acid, EDC, and NHS were 1.8 mol/L, 10 mmol/L, and 18 mmol/L respectively. After 30 minutes at 22° C., 2 mg of ALP (about 18 nmol) and 2 ml of 0.1 M phosphate buffer (pH 7.2) were added. After 3 hours at 22° C., the reaction solution was ultra filtered 3 times in a 15 ml ultrafiltration tube (Millipore Company) whose cut-off molecular weight was 30 kDa, with 30 mM MES buffer (pH 6.0) as a replacement buffer. In this way, unreacted benzoic acid, EDC, NHS, and by-products were removed to obtain a solution of ALP with the amino group blocked.

EDC and NHS were added to 1 ml of a 10 mmol/L solution of ALP with the amino group blocked, wherein the final concentration of EDC and NHS were 10 mmol/L and 20 mmol/L respectively. After 30 minutes at 22° C., mercapto ethanol was added to a final concentration of 10 mM to stop the reaction, yielding a solution of ALP with the carboxyl group activated and the amino group blocked.

Then, 1.5 mg of goat anti-TSH polyclonal antibody (about 10 nmol) and 2 ml of 0.1 M phosphate buffer (pH 7.2) were added to the solution of ALP with the carboxyl group activated and the amino group blocked. After cross-linking for 3 hours at 37° C., the enzyme-antibody conjugate was purified with a Protein G affinity column (GE Company), yielding a solution of goat anti-TSH polyclonal antibody-ALP conjugate.

Example 6

Sodium oxalate was dissolved in 800 µl of 30 mM MES buffer (pH 6.0), EDC and NHS were added, and then buffer was added until the volume of the solution was 1000 µl, wherein final concentrations of sodium oxalate, EDC, and NHS were 1.8 mol/L, 18 mmol/L, and 18 mmol/L respectively. After 30 minutes at 22° C., 2 mg of ALP (about 18 nmol) and 2 ml of 0.1 M phosphate buffer (pH 7.2) were added. After 3 hours at 22° C., the reaction solution was ultra filtered 3 times in a 15 ml ultrafiltration tube (Millipore Company) whose cut-off molecular weight was 30 kDa, with 30 mM MES buffer (pH 6.0) as a replacement buffer. In this way, unreacted sodium oxalate, EDC, NHS, and by-products were removed to obtain a solution of ALP with the amino group blocked.

EDC was added to 1 ml of a 10 mmol/L solution of ALP with the amino group blocked, wherein the final concentration of EDC was 10 mmol/L. After 30 minutes at 22° C., mercapto ethanol was added to a final concentration of 5 mM. A solution of ALP with the carboxyl group activated and the amino group blocked was obtained.

Then, 1 mg of mouse anti-TSH monoclonal antibody (6.67 nmol) and 2 ml of 30 mM MES buffer (pH 6.0) were added to the solution of ALP with the carboxyl group activated and the amino group blocked. After 3 hours at 37° C., the enzyme-antibody conjugate was purified from the solution with a Protein G affinity column (GE Company), yielding a solution of mouse anti-TSH monoclonal antibody-ALP conjugate.

Example 7

With reference to the GA method and the sodium periodate method in Bioconjugate Techniques (Academic Press/2008, the $2^{nd}$ edition), solutions of an anti-TSH antibody-ALP conjugate were prepared. The solutions of anti-TSH antibody-ALP conjugate obtained in Example 1-5, and the antibody-enzyme conjugates obtained by the GA method and the sodium periodate method were used in chemiluminescence enzyme immunoassays of TSH. 50 μg of magnetic beads coated with TSH monoclonal antibody was added to a sample of 10 μU/ml TSH, and then 0.4 pmol anti-TSH antibody-ALP conjugates prepared with the above methods were added respectively. The solution was incubated and rinsed. Then, 200 μl of chemiluminescent substrate solution Lumiphos 530 (obtained from Beckman Coulter, Inc, the same below) was added. Luminescence intensities were measured in triplicate with a Model BHP9507 chemiluminescence immunoassay analyzer (Beijing Hamamatsu Photon Techniques Inc.). The average value for each antibody-enzyme conjugate is shown in Table 1. Higher luminescence intensity indicates higher activity of the enzyme conjugate.

TABLE 1

Comparison results of TSH detection with enzyme conjugates prepared with various methods

| Enzyme Conjugate | Average luminescence intensity |
|---|---|
| Enzyme Conjugate of Example 1 | 1100590 |
| Enzyme Conjugate of Example 2 | 836522 |
| Enzyme Conjugate of Example 3 | 706884 |
| Enzyme Conjugate of Example 4 | 1003046 |
| Enzyme Conjugate of Example 5 | 668521 |
| Enzyme Conjugate of Example 6 | 725664 |
| Enzyme Conjugate obtained with GA Method | 470467 |
| Enzyme Conjugate obtained with sodium periodate method | 456201 |

As shown in Table 1, the activity of enzyme conjugates prepared by the labeling process of the present disclosure is higher than that of the enzyme conjugates prepared by conventional methods.

Example 8

Figure 2:
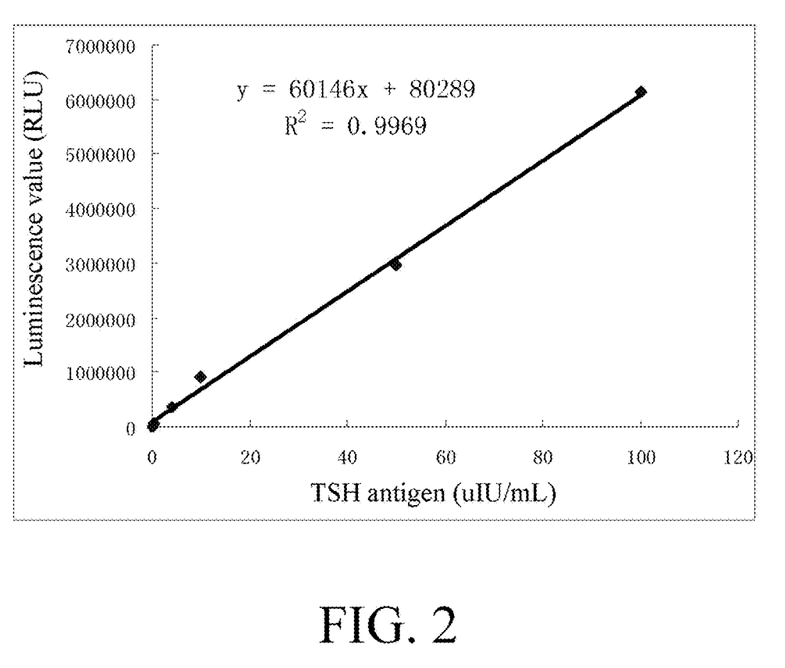
FIG. 2 shows a graph of luminescence intensities for a series of TSH antigen concentrations with a linear regression fit line.

The solution of the goat anti-TSH polyclonal antibody-ALP conjugate obtained in Example 1 was used in chemiluminescence enzyme immunoassays using a series of concentrations of TSH. 50 μg of magnetic beads coated with TSH monoclonal antibody and 0.4 pmol goat anti-TSH polyclonal antibody-ALP conjugate were added to a series of TSH sample solutions. The solution was incubated and then rinsed. Then, 200 μl of chemiluminescent substrate solution Lumiphos 530 was added. Luminescence intensities were measured with a Model BHP9507 chemiluminescence immunoassay analyzer, and the results are shown in Table 2. With the TSH antigen concentration as the X axis and the luminescence intensity as the Y axis, a linear fit of concentration versus luminescence intensity was performed, as shown in FIG. 2.

TABLE 2

Immunoassay results of TSH antigen samples of series concentrations

| Concentration of TSH Antigen | Luminescence Intensity |
|---|---|
| 0 μIU/ml | 5714 |
| 0.1 μIU/ml | 14808 |
| 0.5 μIU/ml | 53322 |
| 4 μIU/ml | 368538 |
| 10 μIU/ml | 931946 |
| 50 μIU/ml | 2951268 |
| 100 μIU/ml | 6136542 |

As shown in Table 2 and FIG. 2, the antibody-enzyme conjugates prepared by the labeling process of the present disclosure can be used in chemiluminescence immunoassay and had good effect. The method for preparing an ALP conjugate of the present disclosure has good applicability.

Example 9

Sodium acetate was dissolved in 800 μl of 30 mM MES buffer (pH 6.0), EDC and NHS were added, and then buffer was added until the volume of the solution was 1000 μl, wherein final concentrations of sodium acetate, EDC, and NHS were 1.8 mol/L, 18 mmol/L, and 18 mmol/L respectively. After 30 minutes at 22° C., 2 mg of ALP (about 18 nmol) and 2 ml of 0.1 M phosphate buffer (pH 7.2) were added. After 3 hours at 22° C., the reaction solution was ultra filtered 3 times in a 15 ml ultrafiltration tube (Millipore Company) whose cut-off molecular weight was 30 kDa, with 30 mM MES buffer (pH 6.0) as a replacement buffer. In this way, unreacted sodium acetate, EDC, NHS, and by-products were removed, to obtain a solution of ALP with the amino group blocked.

EDC and NHS were added to 1 ml of a 10 mmol/L solution of ALP with the amino group blocked, wherein the final concentration of EDC and NHS were 10 mmol/L and 20 mmol/L respectively. After 30 minutes at 22° C., mercapto ethanol was added to a final concentration of 10 mM to stop the reaction, yielding a solution of ALP with the carboxyl group activated and the amino group blocked.

Then, 100 μg of thyroxine (128.7 nmol) which was dissolved in DMSO and 2 ml of 0.1 M HEPES buffer (pH 7.2) were added to the solution of ALP with the carboxyl group activated and the amino group blocked. After 3 hours at 37° C., the reaction solution was ultra filtered 3 times in a 15 ml ultrafiltration tube (Millipore Company) whose cut-off molecular weight was 30 kDa, with 50 mM tris(hydroxymethyl)aminomethane (TRIS) buffer (pH 7.5) as a replacement buffer. An ALP-thyroxine conjugate (conjugate of new method) was obtained.

With reference to the GA method in Bioconjugate Techniques (Academic Press/2008, the $2^{nd}$ edition), an ALP-thyroxine conjugate (conjugate of GA method) was prepared.

The conjugate solutions obtained by the new method and the GA method were used in chemiluminescence enzyme immunoassays of thyroxine. 0.4 pmol ALP-thyroxine conjugates prepared with these two method were respectively added to 50 μg of magnetic beads coated with anti-thyroxine polyclonal antibody. The solution was incubated and rinsed. Next, 200 μl of chemiluminescent substrate solution Lumiphos 530 was added, and luminescence intensities were measured with a Model BHP9507 chemiluminescence immunoassay analyzer, as shown in Table 3. Higher luminescence intensity indicates higher activity of the enzyme conjugate.

TABLE 3

Comparison results of thyroxine detection with enzyme conjugates prepared by new and GA method

| Enzyme Conjugate | Luminescence Intensity |
|---|---|
| Conjugate of new method | 2154124 |
| Conjugate of GA Method | 532457 |

As shown in Table 3, the activity of enzyme conjugates prepared by the labeling process of the present disclosure is higher than that of the enzyme conjugate prepared by the GA cross-linking method.

What is claimed is:

1. A method for preparing a conjugate of a first substance to be conjugated and a second substance to be conjugated, the method comprising:
   1) providing a first substance to be conjugated, wherein the first substance to be conjugated has a reactive amino group and a reactive carboxyl group and is an enzyme for labeling, selected from at least one of the following: alkaline phosphatase (ALP), horseradish peroxidase, β-galactosidase, urease, glucose-6-phosphate dehydrogenase, glucose oxidase, and malate dehydrogenase;
   2) providing a second substance to be conjugated, wherein the second substance to be conjugated has a reactive amino group;
   3) reacting a reactive amino group of the first substance to be conjugated with an amino group blocking agent that is a carboxyl compound having General Formula I, in the presence of a first cross-linking agent, to obtain a first substance to be conjugated having a blocked amino group:

Formula I wherein $R_1$ is selected from at least one of following: H, $C_{1-6}$ alkyl, $C_nH_{2n}COOH$, phenyl, and phenyl$C_{1-6}$ alkyl, wherein n is an integer of 0-4, and phenyl or phenyl$C_{1-6}$ alkyl is optionally and independently substituted with a substitution group selected from at least one of the following: halogen, hydroxyl, mercapto, cyano, nitro, alkyl, aryl, alkoxy, heterocyclyl, haloalkyl, and carboxyl; and
   $R_2$ is a group which is capable of dissociating in water; and wherein
   the first cross-linking agent comprises a carbodiimide and, optionally, a hydroxysuccinimide;
   4) optionally quenching the first cross-linking agent with a mercapto compound;
   5) purifying the first substance to be conjugated having a blocked amino group;
   6) reacting a second cross-linking agent with a reactive carboxyl group of the first substance to be conjugated having a blocked amino group, to create an activated first substance to be conjugated having a blocked amino group, wherein the second cross-linking agent comprises a carbodiimide and, optionally, a hydroxysuccinimide;
   7) cross-linking the activated first substance to be conjugated having a blocked amino group, with a reactive amino group of the second substance to be conjugated to obtain a conjugate; and
   8) optionally quenching the second cross-linking agent with a mercapto compound.

2. The method according to claim 1, wherein the second substance to be conjugated is a peptide or a protein.

3. The method according to claim 2, wherein the second substance to be conjugated is a targeting moiety selected from at least one of the following: an antibody and a ligand.

4. The method according to claim 1, wherein the second substance to be conjugated is a hapten.

5. The method according to claim 1, wherein the second substance to be conjugated is an amino group containing surface that is a solid phase.

6. The method according to claim 1, wherein the second substance to be conjugated is a drug containing an amino group.

7. The method according to claim 1, wherein the purification step comprises one or more of: ultrafiltration purification, desalting column purification, or dialysis purification.

8. The method according to claim 1, wherein after activation of the carboxyl group of the first substance to be conjugated having a blocked amino group,
   the activity of the second crosslinking agent is quenched by adding a mercapto compound, or
   the second crosslinking agent is removed through purification,
   yielding the first substance to be conjugated with the carboxyl group activated and having a blocked amino group.

9. The method according to claim 8, wherein the mercapto compound is selected from at least one of the following: mercapto ethanol and mercapto threitol.

10. The method according to claim 8, wherein the first substance to be conjugated with the carboxyl group activated and having a blocked amino group, is purified through one or more of ultrafiltration purification, desalting column purification, or dialysis purification.

11. The method according to claim 1, wherein the carboxyl compound is selected from at least one of the following: formic acid, acetic acid, oxalic acid, benzoic acid, salicylic acid, and sulfosalicylic acid, or a salt thereof.

12. The method according to claim 1, wherein the carbodiimide is selected from at least one of the following: dicyclohexylcarbodiimide, 1-(3-dimethylaminopropyl)-3-ethylcarbodiimide, and N,N'-diisopropylcarbodiimide; and the hydroxysuccinimide is selected from at least one of the following: N-hydroxysucciniimde and sulfo-N-hydroxysuccinimide.

13. The method according to claim 1, wherein in Step 3), the molar excess of the carboxyl compound is 500-200000 times that of the first substance to be conjugated.

14. The method according to claim 1, wherein in Step 3), the molar excess of the cross-linking agent is 50-5000 times that of the first substance to be conjugated.

15. The method according to claim 1, wherein in Step 3), the molar ratio of the carbodiimide to the hydroxysuccinimide is in a range of 5:1 to 1:10.

16. The method according to claim 1, wherein in Step 6), the molar excess of the carbodiimide is 10-5000 times that of the first substance to be conjugated having a blocked amino group.

17. The method according to claim 1, wherein in Step 6), the molar ratio of the carbodiimide to the hydroxysuccinimide is in a range of 5:1 to 1:10.

18. A kit for preparing a conjugate between an enzyme and a substance having a reactive amino group, or a substance to which a reactive amino group is introduced through modification, comprising:
1) an enzyme for labeling, selected from at least one of the following: alkaline phosphatase (ALP), horseradish peroxidase, β-galactosidase, urease, glucose-6-phosphate dehydrogenase, glucose oxidase, and malate dehydrogenase;
2) an amino group blocking agent for blocking reactive amino groups on the enzyme, said amino group blocking agent being a carboxyl compound having General Formula I:

Formula I where $R_1$ is selected from at least one of the following: H, $C_{1-6}$ alkyl, $C_nH_{2n}COOH$, phenyl, and phenyl$C_{1-6}$ alkyl, wherein n is an integer of 0-4, and phenyl or phenyl$C_{1-6}$ alkyl is optionally and independently substituted with a substitution group selected from at least one of the following: halogen, hydroxyl, mercapto, cyano, nitro, alkyl, aryl, alkoxy, heterocyclyl, haloalkyl, and carboxyl; and $R_2$ is a group which is capable of dissociating in water;
3) a cross-linking agent, said cross-linking agent being a carbodiimide and, optionally, a hydroxysuccinimide; and
4) an optional cross-linking agent quenching agent, said quenching agent being a mercapto compound.

19. The kit according to claim 18, wherein the carboxyl compound is selected from at least one of the following: formic acid, acetic acid, oxalic acid, benzoic acid, salicylic acid, and sulfosalicylic acid, or a salt thereof.

20. The kit according to claim 18, wherein the carbodiimide is selected from at least one of the following: dicyclohexylcarbodiimide, 1-(3-dimethylaminopropyl)-3-ethylcarbodiimide, and N,N'-diisopropylcarbodiimide; and the hydroxysuccinimide is selected from at least one of the following: N-hydroxysuccinimide and sulfo-N-hydroxysuccinimide.

21. The kit according to claim 18, wherein the mercapto compound is selected from at least one of the following: mercapto ethanol and mercapto threitol.

22. The kit according to claim 18, wherein the kit further comprises at least one of: an ultrafiltration tube, or instructions for operators.

* * * * *